US00PP33762P2

(12) United States Plant Patent
Danziger

(10) Patent No.: US PP33,762 P2
(45) Date of Patent: Dec. 21, 2021

(54) ***ACHILLEA* PLANT NAMED 'DACHFULMON'**

(50) Latin Name: *Achillea ptarmica*
Varietal Denomination: DACHFULMON

(71) Applicant: Danziger 'DAN' Flower Farm, Beit Dagan (IL)

(72) Inventor: Gavriel Danziger, Beit Dagan (IL)

(73) Assignee: Danziger "Dan" Flower Farm

( * ) Notice: Subject to any disclaimer, the term of this patent is extended or adjusted under 35 U.S.C. 154(b) by 0 days.

(21) Appl. No.: 17/330,113

(22) Filed: May 25, 2021

(51) Int. Cl.
*A01H 5/02* (2018.01)
*A01H 6/14* (2018.01)

(52) U.S. Cl.
USPC ..... Plt./263.1
CPC ..... *A01H 6/14* (2018.05)

(58) Field of Classification Search
USPC ..... Plt./263.1
CPC ..... A01H 6/14; A01H 5/02
See application file for complete search history.

*Primary Examiner* — Keith O. Robinson
(74) *Attorney, Agent, or Firm* — Cassandra Bright

(57) ABSTRACT

A new and distinct variety of *Achillea* plant named 'DACHFULMON' is disclosed, characterized by an upright plant habit between 80 and 120 cm. Plants produce abundant large white flowers. Plants produce flowering stems for cut flower use. The new variety is a *Achillea*, useful for ornamental horticulture purposes.

2 Drawing Sheets

Latin name of the genus and species: *Achillea ptarmica.*
Variety denomination: 'DACHFULMON'.

BACKGROUND OF THE INVENTION

The new *Achillea* cultivar is a product of a planned breeding program. The new variety was discovered as a seedling resulting from a bulk open-pollination and bulk seed collection program at a research greenhouse in Moshav Mishmar Hashiva, Israel. The interesting new variety was discovered during the Spring of 2019.

The parent varieties are unknown as breeding blocks were set up for open-pollination and bulk collection of seeds.

Asexual reproduction of the new cultivar has been performed by terminal vegetative cuttings. This was first performed at a research greenhouse in Moshav Mishmar Hashiva, Israel during the Spring of 2019 and has shown that the unique features of this cultivar are stable and reproduced true to type in more successive generations.

SUMMARY OF THE INVENTION

The cultivar 'DACHFULMON' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DACHFULMON'. These characteristics in combination distinguish 'DACHFULMON' as a new and distinct *Achillea* cultivar:

1. Plant height between 80 and 120 cm.
2. Upright plant habit.
3. Flower diameter between 1.2 to 2.5 cm.
4. Usefulness for cut flower production.

PARENTAL COMPARISON

Parent varieties are unknown.

COMMERCIAL COMPARISON

Plants of the new cultivar 'DACHFULMON' are comparable to the unpatented commercial variety *Achillea* 'Summer Drift'. The two *Achillea* varieties are similar in most horticultural characteristics; however, the new variety 'DACHFULMON' differs in the following:

1. Plant height of the new variety is 80 to 120 cm; plant height of this comparator is about 30 cm.
2. The new variety has an upright plant habit; this comparator has a semi-trailing plant habit.

Plants of the new cultivar 'DACHFULMON' can also be compared to the unpatented commercial variety *Achillea* 'The Pearl'. The two *Achillea* varieties are similar in most horticultural characteristics; however, the new variety 'DACHFULMON' differs in the following:

1. Plants of the new variety produce many more flowers than plants of this comparator.
2. Inflorescences of the new variety have more flowers per inflorescence, with flowers occurring both apically and laterally on the inflorescence. Inflorescences of this comparator have flowers mainly on the top.
3. Flowering stems of the new variety are sturdier than flowering stems of this comparator.
4. Flowers of the new variety are up to twice as wide as flowers of this comparator.

BRIEF DESCRIPTION OF THE PHOTOGRAPHS

Figure 1:
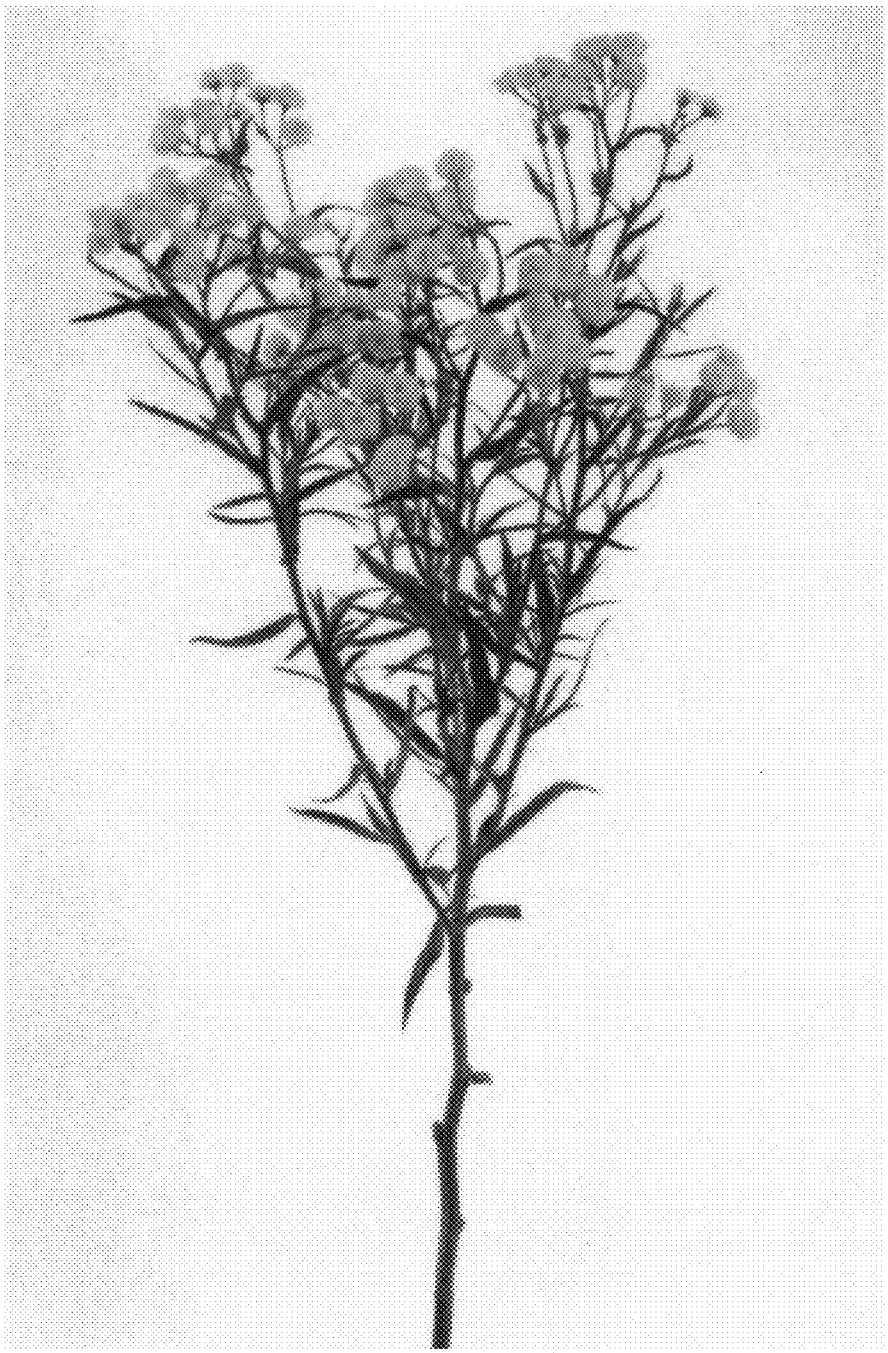

The accompanying photograph in FIG. 1 illustrates in full color a typical flowering stem of 'DACHFULMON'.

Figure 2:
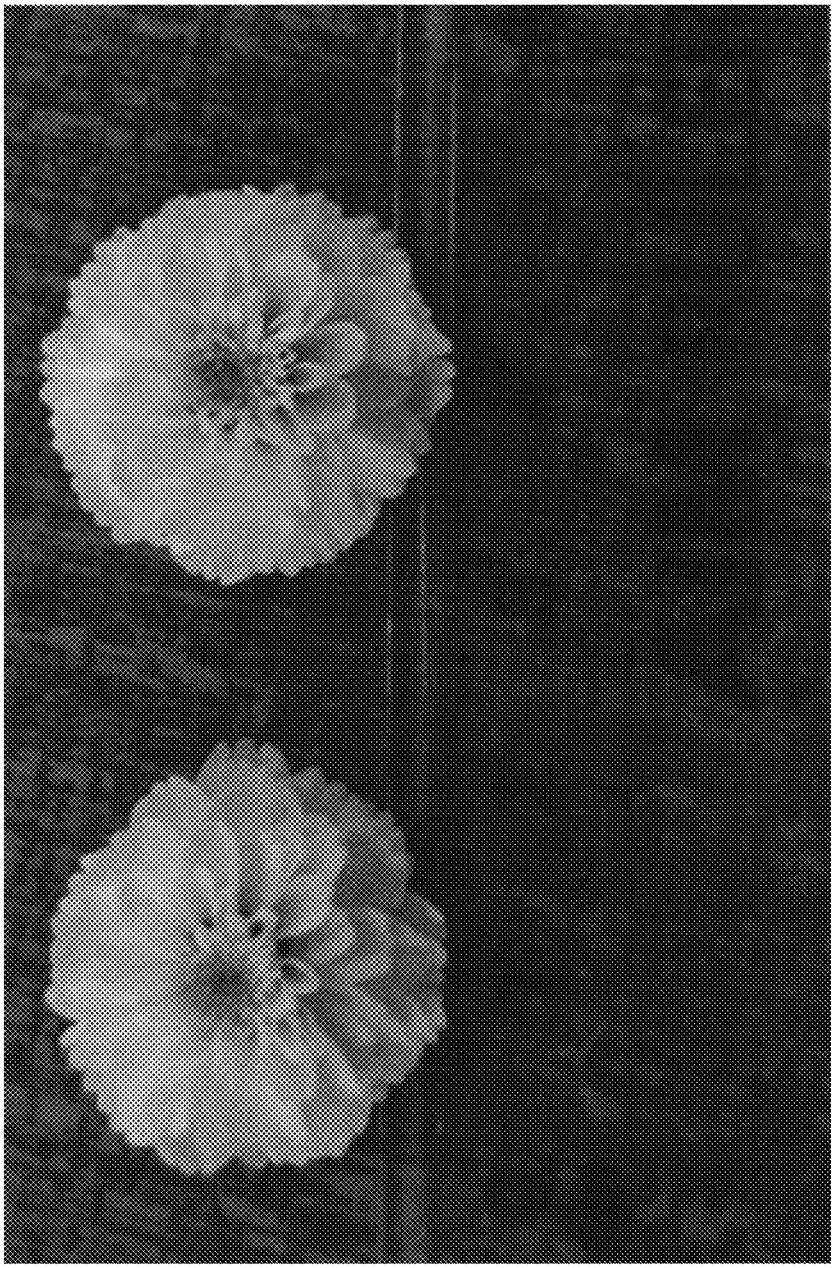

FIG. 2 illustrates a close up of flowers of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'DACHFULMON' plants grown outdoors between December and April of 2021 in Mishmar Hashiva, Israel. The growing temperature ranged from approximately 10° C. to 28° C. during the day and from approximately 6° C. to 18° C. during the night. General light conditions are normal sunlight and numerical values represent averages of typical plant types. Measurements were taken during May of 2021.

Botanical classification: *Achillea ptarmica* 'DACHFULMON'.

PROPAGATION

Type of propagation typically used: Vegetative terminal cuttings.

Time to initiate roots: About 7 to 14 days at approximately 24° C.

Time to produce a rooted cutting or liner: About 14-21 days at approximately 24° C.

PLANT

Type: Flowering perennial used for cut flower production, or ornamental landscape.

Age of plant described: Approximately 90 days from rooted cutting, planted in the ground.

Overall plant growth habit: Upright.

Height: To top of foliage: approximately 90 cm. To top of flowers: approximately 100 cm.

Plant spread: Approximately 20 cm.

Growth rate: Moderate to rapid.

Characteristics of main stems:

*Shape/form.*—Ridged.
*Length.*—Approximately 80-120 cm.
*Diameter.*—Approximately 0.8 cm.
*Color.*—Close to RHS Yellow-Green 144A.
*Texture.*—Glabrous.
*Strength.*—Moderate.
*Internode length.*—Approximately 1.5 cm.

Root description: Fibrous, color white to cream, not accurately measured with RHS chart.

Rhizomes: Not observed.

FOLIAGE

Leaf:

Leaf:

*Arrangement.*—Simple, alternate.
*Average length.*—Approximately 8.5 to 10 cm.
*Average width.*—Approximately 1.2 to 0.5 cm.
*Shape of blade.*—Falcate.
*Apex.*—Acuminate.
*Base.*—Cuneate.
*Attachment.*—Sessile.
*Margin.*—Serrulate.
*Texture of top surface.*—Glabrous.
*Texture of bottom surface.*—Glabrous.
*Appearance of top surface.*—Matte.
*Appearance of bottom surface.*—Matte.
*Leaf internode length.*—Approximately 2 cm.
*Color.*—Young foliage upper side: Near RHS Green 137C. Young foliage under side: Near RHS Green 138A. Mature foliage upper side: Near RHS Green N137C. Mature foliage under side: Near RHS Green 139A.
*Venation.*—Type: Pinnate. Venation color upper side: Near RHS Green 137C. Venation color under side: Near RHS Green 139B.

FLOWER

Natural flowering season: Spring.

Inflorescence type and habit: Panicle composed of composite flowers.

Vase life: Approximately 14 days.

Quantity of flowers: About 100-170 flowers per plant.

Inflorescence size:

*Height.*—Approximately 35 to 75 cm.
*Diameter.*—Approximately 10 to 15 cm.

Individual flowers:

Size:

*Diameter.*—Approximately 1.2 cm to 2.5 cm.
*Length.*—Approximately 1 cm to 1.3 cm.
*Persistence.*—Self-cleaning.
*Fragrance.*—Light.

Ray florets:

*Number of ray florets.*—Average 124.
*Length.*—Approximately 5 mm.
*Width.*—Approximately 5 mm.
*Apex shape.*—Double emarginate.
*Margin.*—Entire.

Color:

Ray florets:

*Upper surface at first opening.*—Near White NN155D.
*Upper surface at maturity.*—Near White NN155D.
*Upper surface at fading.*—Near White NN155B.
*Under surface at first opening.*—Near White NN155B.
*Under surface at maturity.*—Near White NN155C.
*Under surface at fading.*—Near White NN155B.

Disc florets:

*Number of disc florets.*—Average 1-4.
*Length.*—Approximately 1 mm.
*Width.*—Approximately 1 mm.
*Shape.*—Tubular.
*Margin.*—Entire.
*At first opening.*—Near White NN155B.
*At maturity.*—Near White NN155B.
*At fading.*—Near White NN155B.

Phyllaries:

*Number.*—Average 29.
*Length.*—Approximately 2 to 4 mm.
*Width.*—Approximately 1.0 to 1.5 mm.
*Shape.*—Sickle-shaped.
*Texture.*—Hirsute.
*Apex shape.*—Acuminate.
*Margin.*—Toothed.
*Color.*—Near Green 141B.

Bud:

*Shape.*—Oblate.
*Length.*—Approximately 3 mm.
*Diameter.*—Approximately 4 mm.
*Color.*—Near Green 141B.

Peduncle:
*Length.*—Approximately 4 to 7 cm.
*Diameter.*—Approximately 2 mm.
*Texture.*—Hirsute.
*Color.*—Near Green 143B.
*Orientation.*—About 30° from center.
*Strength.*—Moderate.
Pedicel:
*Length.*—3 to 10 mm.
*Diameter.*—1 mm.
*Texture.*—Somewhat hirsute.
*Color.*—Near Green 143B.
*Angle.*—Average angle 30°.
*Strength.*—Moderate.

REPRODUCTIVE ORGANS

Present only in Androecium:
Stamens:
*Number.*—8.
Anthers:
*Shape.*—ovoid.
*Length.*—Approximately 0.2 mm.
*Color.*—21a RHS.
*Pollen.*—Color: 21a RHS. Quantity: moderate.
Gynoecium:
Pistil:
*Number.*—1.
*Length.*—Approximately 0.5 mm.
*Style.*—Length: Approximately 0.3 mm. Color: White 155A.
*Stigma.*—Shape: Basifixed. Color: White 155A. Ovary Color: Yellow-Green 149C.

OTHER CHARACTERISTICS

Fruits and seeds: Not observed to date.
Disease/pest resistance: Neither resistance nor susceptibility to normal diseases of *Achillea ptarmica* observed.
Temperature tolerance: Low temperature tolerance not observed, typically *Achillea ptarmica* tolerate temperatures in USDA zones 3-9.

What is claimed is:

1. A new and distinct cultivar of *Achillea* plant named 'DACHFULMON' as herein illustrated and described.

* * * * *